US010716892B2

(12) United States Patent
Auld et al.

(10) Patent No.: US 10,716,892 B2
(45) Date of Patent: Jul. 21, 2020

(54) SELF-POWERED SYRINGE DRIVERS

(71) Applicant: ALTAVIZ, LLC, Irvine, CA (US)

(72) Inventors: Jack R. Auld, Laguna Niguel, CA (US); Matthew Flowers, Aliso Viejo, CA (US); Matthew McCawley, San Clemente, CA (US); John C. Huculak, Mission Viejo, CA (US); Andrew Scheiber, Laguna Niguel, CA (US); James Lescoulie, Costa Mesa, CA (US)

(73) Assignee: ALTAVIZ, LLC, Irvine, CA (US)

( * ) Notice: Subject to any disclaimer, the term of this patent is extended or adjusted under 35 U.S.C. 154(b) by 262 days.

(21) Appl. No.: 15/582,731

(22) Filed: Apr. 30, 2017

(65) Prior Publication Data

US 2017/0312422 A1 Nov. 2, 2017

Related U.S. Application Data

(60) Provisional application No. 62/329,910, filed on Apr. 29, 2016, provisional application No. 62/453,947, filed on Feb. 2, 2017.

(51) Int. Cl.
*A61M 5/14* (2006.01)
*A61M 5/145* (2006.01)
(Continued)

(52) U.S. Cl.
CPC ........ *A61M 5/1456* (2013.01); *A61M 5/1454* (2013.01); *A61M 5/2053* (2013.01);
(Continued)

(58) Field of Classification Search
CPC .... A61M 2005/206; A61M 2005/2013; A61M 5/24; A61M 5/2046; A61M 5/178; A61M 5/2053
See application file for complete search history.

(56) References Cited

U.S. PATENT DOCUMENTS 3,474,787 A * 10/1969 Grant ...................... A61M 5/20
604/135
4,284,077 A * 8/1981 Wagner ................... A61M 5/20
604/115
(Continued)

FOREIGN PATENT DOCUMENTS

WO 2004067067 A1 8/2004
WO 2005075009 A1 8/2005

OTHER PUBLICATIONS

PCT International Search Report and Written Opinion for PCT/US2017030310, Applicant: Alraviz, LLC, Forms PCT/ISA/220, PCT/ISA/210, and PCT/ISA/237; dated Aug. 14, 2017, 20 pages.

*Primary Examiner* — Scott J Medway
(74) *Attorney, Agent, or Firm* — William A. English; Vista IP Law Group LLP

(57) ABSTRACT

Devices and methods are provided for delivering fluid into a patient's body. In an exemplary embodiment, the device may include a syringe cartridge and a syringe driver that may be coupled to the cartridge. The cartridge may include a housing including a proximal end, a distal end, and defining an interior, the cartridge further including a piston slidably disposed within the interior for delivering fluid within the interior through a port in the distal end. The driver may include a plunger for advancing the piston within the interior of the housing, a source of pressurized fluid, a valve, and an actuator member coupled to the valve for selectively opening a flow path from the source to the plunger to control flow of the pressurized fluid to advance the plunger to deliver fluid from the interior of the housing at a desired rate.

22 Claims, 13 Drawing Sheets

(51) Int. Cl.
*A61M 5/20* (2006.01)
*A61M 5/24* (2006.01)
*A61M 5/48* (2006.01)

(52) U.S. Cl.
CPC .............. *A61M 5/24* (2013.01); *A61M 5/482* (2013.01); *A61M 5/484* (2013.01); *A61M 5/488* (2013.01); *A61M 2005/14506* (2013.01); *A61M 2205/128* (2013.01); *A61M 2207/00* (2013.01)

(56) References Cited

U.S. PATENT DOCUMENTS

| | | | | |
|---|---|---|---|---|
| 5,180,371 | A | * | 1/1993 | Spinello ................. A61C 19/08 604/118 |
| 5,312,335 | A | * | 5/1994 | McKinnon .............. A61M 5/24 604/68 |
| 5,383,851 | A | * | 1/1995 | McKinnon, Jr. ........ A61M 5/30 604/143 |
| 2002/0055712 | A1 | * | 5/2002 | Neracher ............ A61M 5/2053 604/143 |
| 2002/0188251 | A1 | * | 12/2002 | Staylor ................... A61M 5/30 604/70 |
| 2003/0233070 | A1 | | 12/2003 | De La Serna et al. |
| 2005/0070848 | A1 | * | 3/2005 | Kim .................... A61M 5/2053 604/140 |
| 2006/0052753 | A1 | | 3/2006 | Mansouri |
| 2008/0114295 | A1 | * | 5/2008 | Glynn .................... A61M 5/24 604/110 |
| 2010/0094214 | A1 | * | 4/2010 | Abry ................... A61M 5/2033 604/110 |
| 2010/0130930 | A1 | * | 5/2010 | Stamp ................. A61M 5/2033 604/135 |
| 2011/0301538 | A1 | * | 12/2011 | Stammen .............. A61M 5/145 604/121 |
| 2013/0317478 | A1 | * | 11/2013 | Auld ................... A61M 5/2046 604/506 |
| 2014/0114248 | A1 | | 4/2014 | DeSalvo et al. |
| 2015/0282928 | A1 | | 10/2015 | Auld et al. |
| 2016/0361496 | A1 | | 12/2016 | Guillermo et al. |
| 2017/0119522 | A1 | | 5/2017 | Auld et al. |
| 2017/0258583 | A1 | | 9/2017 | McCawley et al. |

* cited by examiner

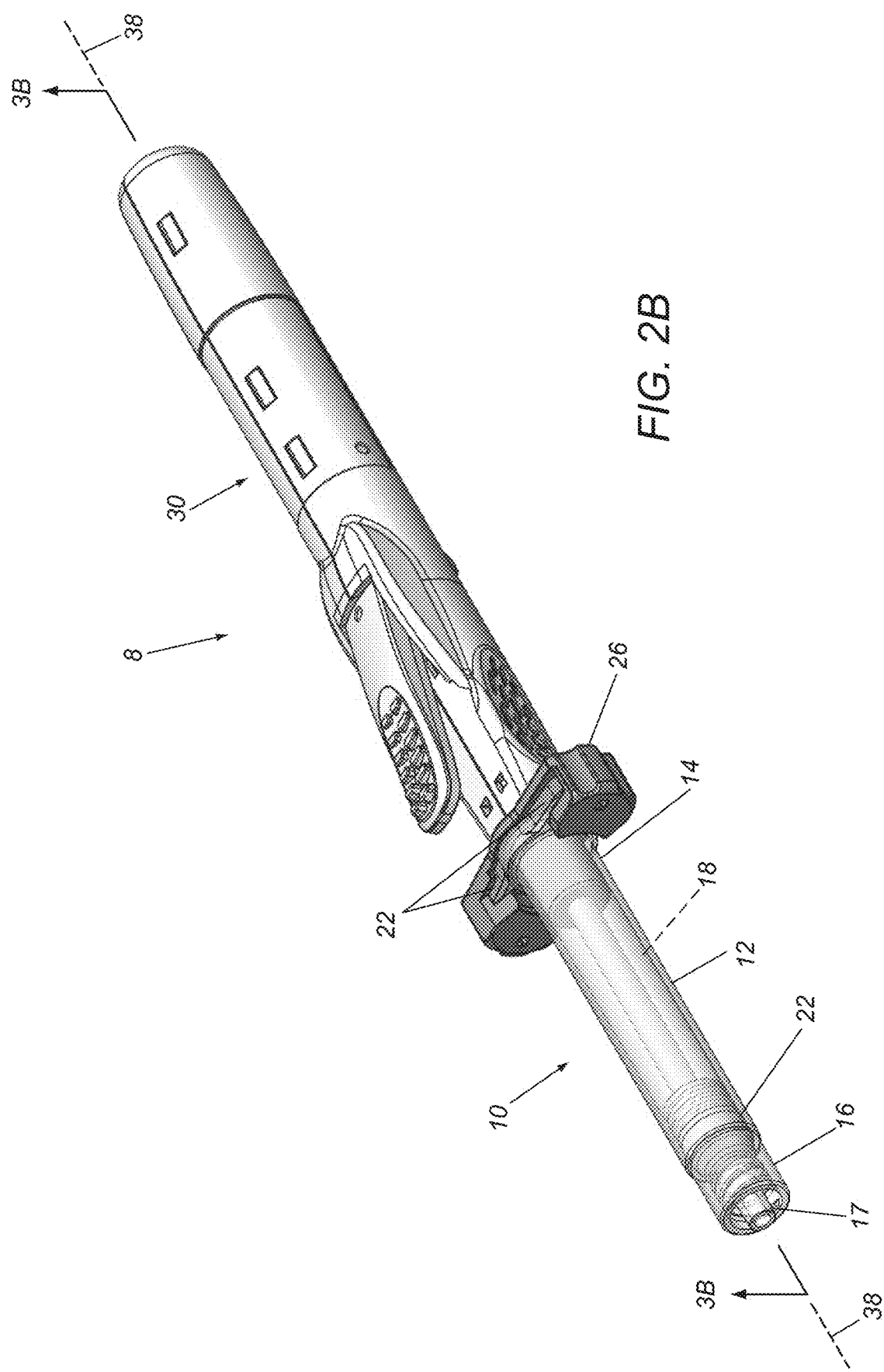

SELF-POWERED SYRINGE DRIVERS

RELATED APPLICATION DATA

The present application claims benefit of U.S. provisional application Ser. No. 62/329,910, filed Apr. 29, 2016, and 62/453,947, filed Feb. 2, 2017, the entire disclosures of which are expressly incorporated by reference herein.

TECHNICAL FIELD

The inventions described herein generally relate to devices and methods for delivering fluids and, more particularly, to self-powered syringe drivers for syringe devices, e.g., for delivering fluids into a patient's body, and to methods for using such devices.

BACKGROUND

There are many applications requiring controlled delivery of a medicament or viscous fluid while maintaining precise position control of the delivery needle to deliver a precise volume of fluid in a precise location. In many of these cases, the desired therapeutic effect is completely dependent on meeting all of these objectives.

In particular, during delivery of various fluids into a patient's body using a syringe and needle, it is generally desirable for a clinician to accurately position the tip of the needle, apply force to the syringe's plunger to develop desired flow of the therapeutic fluid, and control the flow rate of the fluid. For highly viscous fluids, the forces required to develop the fluid flow can be very high requiring significant hand strength on the part of the clinician. In most cases, fine position control is also required. Typical syringes are held and actuated at the end completely opposite to the end that discharges the fluid, which makes it difficult to maintain positional accuracy of the tip. Typically, the clinician uses the same hand to position the syringe that is used to develop and control the flow. Fine motor skills are preferred for controlling the position and flow rate, while gross motor skills are required for developing flow and maintaining flow rate in viscous materials, and, consequently, current syringe and needle systems compromise these skills.

Therefore, devices and methods for delivering fluids into a patient's body with increased precision and/or control would be useful.

SUMMARY

The inventions disclosed herein generally relate to devices and methods for delivering fluids and, more particularly, to self-powered syringe drivers for syringe devices, e.g., for delivering fluids into a patient's body, and to methods for using such devices.

In exemplary embodiments, the self-powered syringe drivers described herein may include one or more of the following characteristics: 1) provide high delivery pressures necessary to develop adequate flow rates to deliver viscous fluids, 2) provide fine, variable control of delivery flow rate with low actuation forces, 3) enable the device to be held in a manner that provides good control over the position of the delivery tip, 4) provide for limiting the peak flow rate of fluid, 5) provide a self-contained energy source to allow the device to be self-contained, 6) provide a device constructed of low cost materials to enable the device to be single use, and 7) provide options for multiple configurations.

For example, the syringe/needle systems described herein may be relatively low cost, which enable the devices to be used one time to eliminate the need for resterilization and/or reduce the risk of cross contamination between patients, and/or may provide the clinician with flexibility of configuration combination of needle and syringe size.

Generally, the syringe driver is a self-powered device that uses gas pressure to pressurize a substantially incompressible fluid. The flow of the pressurized, incompressible fluid is used to drive a downstream actuator that pushes the syringe plunger through a syringe cartridge to deliver fluid into the body. The speed of delivery may be modulated by controlling the flow of fluid through a variable flow control valve. Since the fluid is substantially incompressible, the speed of the actuator may be assumed to be directly proportional to the flow of fluid through the controller and there is no potential energy stored in the fluid as it is pressurized, providing good control of the syringe plunger without continued travel when the flow control valve is closed.

In an exemplary embodiment, the syringe driver may include one or more of a self-contained pressurized gas container or other energy storage device; an element for puncturing the gas container to charge a pressure chamber; a movable piston in an accumulator that communicates the gas pressure to a volume of fluid; a flow controller in communication with the pressurized fluid to vary the flow rate of the fluid from no flow to maximum flow; a handle, lever, or other actuator to actuate the controller; an actuation cylinder in communication with the fluid downstream of the flow controller to convert the flow of liquid to mechanical motion; a plunger mechanically connected to the actuation cylinder to transmit the actuation force to the syringe plunger; and a receiver to accept a syringe cartridge. In one embodiment, the flow controller may be a needle valve, pressure compensated flow control valve, pressure regulator, or any other suitable element for controlling the flow.

Optionally, the output flow of the controller relative to the input force or position may be linear, exponential, polynomial, or any other suitable profile. In another option, the output flow may be controlled by modulating the pressure of the gas applied to the fluid.

In accordance with another embodiment, a device is provided for delivering a medicament into a patient's body that includes a syringe cartridge comprising a housing including a proximal end, a distal end, and defining an interior, the cartridge further comprising a piston slidably disposed within the interior for delivering a medicament within the interior through a port in the distal end; and a syringe driver comprising a plunger for advancing the piston within the interior of the housing, a source of pressurized fluid, a valve, and an actuator member coupled to the valve for selectively opening a flow path from the source to the plunger to control flow of the pressurized fluid to advance the plunger to deliver medicament from the interior of the housing at a desired rate.

In accordance with still another embodiment, a device is provided for delivering medicament into a patient's body that includes a syringe cartridge and a syringe driver. The syringe cartridge may include a housing including a proximal end, a distal end, and defining an interior; and a piston slidably disposed within the interior for delivering medicament within the interior through a port in the distal end. The syringe driver may include a plunger for advancing the piston within the interior of the housing; an incompressible fluid; an accumulator for applying a predetermined pressure and/or force to the incompressible fluid; and an actuator comprising a valve for selectively opening a flow path to control flow of the incompressible fluid to advance the plunger and deliver medicament from the interior of the housing in a desired manner.

In accordance with yet another embodiment, a device is provided for injecting fluid into a body that includes a syringe cartridge comprising a delivery piston movable within the cartridge for delivering fluid therein into a body; and a syringe driver comprising means for pressurizing an incompressible liquid, means for controlling a flow rate of the liquid, means to limit a peak flow rate of the liquid, an actuator piston that may be coupled to the delivery piston, and an actuator to provide a force to drive the actuator piston based on the flow rate of the liquid.

In accordance with another embodiment, a method is provided for preparing a syringe device that includes providing a syringe cartridge comprising a housing including a proximal end, a distal end, and defining an interior, and a piston slidably disposed within the interior for delivering medicament within the interior through a port in the distal end; and coupling a syringe driver to the proximal end of the syringe cartridge, the syringe driver comprising a plunger for advancing the piston within the interior of the housing, an incompressible fluid, an accumulator for applying a predetermined pressure and/or force to the incompressible fluid, and an actuator comprising a valve for selectively opening a flow path to control flow of the incompressible fluid to advance the plunger and deliver medicament from the interior of the housing in a desired manner.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIGS. 2A and 2B are perspective views of an exemplary embodiment of a syringe device before and after actuation of the device to deliver fluid into a patient's body, respectively.

DETAILED DESCRIPTION OF THE EXEMPLARY EMBODIMENTS

Figure 1:
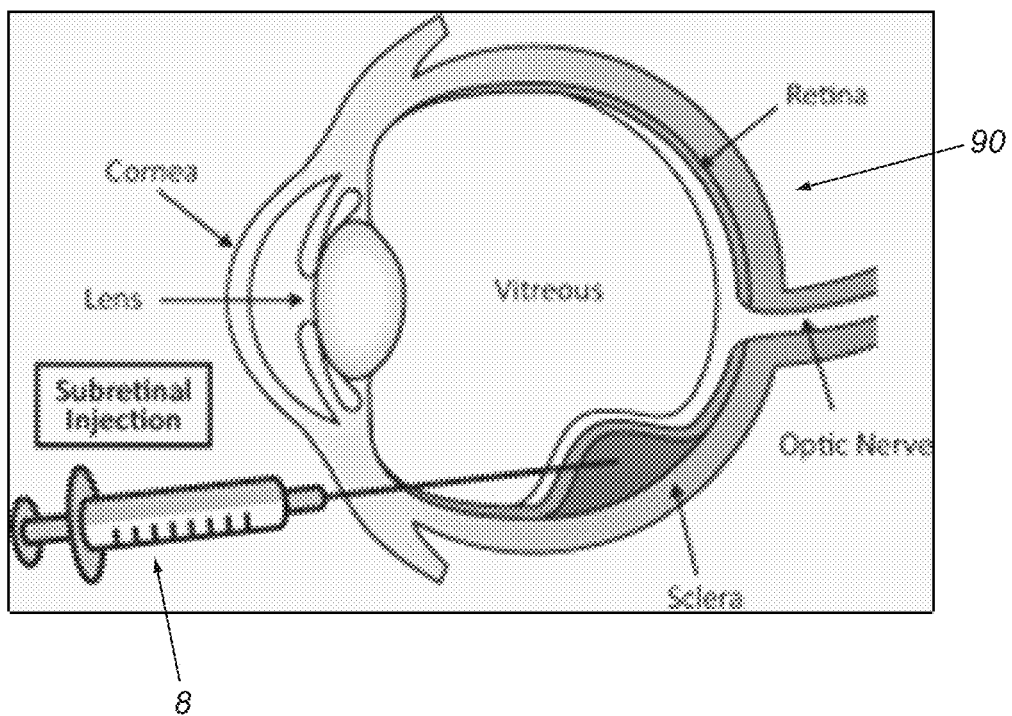
FIG. 1 is an enlarged cross-sectional view of a human eye showing administration of a sub-retinal injection to the eye using a syringe device.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary, or the following detailed description.

Certain terminology may be used in the following description for the purpose of reference only, and thus are not intended to be limiting. For example, terms such as "upper," "lower," "above," and "below" refer to directions in the drawings to which reference is made. Terms such as "proximal," "distal," "front," "back," "rear," and "side" describe the orientation and/or location of portions of the component within a consistent but arbitrary frame of reference, which is made clear by reference to the text and the associated drawings describing the component under discussion. Such terminology may include the words specifically mentioned above, derivatives thereof, and words of similar import.

For example, as used herein, the terms "front" and "distal" refer to parts of the subject device that are located further away from the user (e.g., clinician) of the device, e.g., during an injection operation. As used herein, the terms "rear" and "proximal" refer to the parts of the device that are located closer to the user (e.g., clinician) of the device, e.g., during an injection operation.

There are many applications where controlled delivery of a medicament is desired while maintaining precise position control of the delivery needle to deliver a precise volume of fluid in a precise location. The devices and methods described herein may facilitate precise delivery of medicaments into a patient's body, e.g., one or more viscous fluids or other flowable material for various therapeutic and/or diagnostic purposes. As used herein, "medicament" is intended to refer to any such fluids or materials, such as those described in the examples herein. For example, below is a summary of exemplary applications where the devices and methods described herein may be used to deliver fluids into a patient's body.

Ophthalmology: As shown in FIG. 1, a syringe device 8 may be used for sub-retinal injections in the treatment of several disease conditions of an eye 90. The syringe device 8 may include a syringe cartridge and a syringe driver (not shown), similar to any of the embodiments described herein.

Treatment of retinal vein occlusions: Multiple indications may be treated by the administration of therapeutic agents into the sub-retinal space in the eye. In cases of branch retinal vein occlusion (BRVO) and central retinal vein occlusion (CRVO), 50 to 150 µL of tissue plasminogen activator (TPA) may be administered through relatively small hypodermic needles (e.g., not more than 41 gauge) to dissolve blood clots formed by sub-retinal hemorrhages during the course of retinal surgery. In these cases, the ophthalmic surgeon may place the tip under the surface of a patient's retina and slowly inject the TPA to create a bleb of medicament that dissolves the coagulated blood over the course of a few days.

Gene therapy for the treatment of macular degeneration: Age-related macular degeneration (AMD) is a leading cause of vision loss and blindness among the elderly. AMD is a progressive ocular disease of the part of the retina, called the macula, which enables people to read, visualize faces, and drive. The disease initially causes distortion in central vision, and eventually leads to legal blindness. A layer of cells at the back of the eye, called the retinal pigment epithelium (RPE), provides support, protection, and nutrition to the light sensitive cells of the retina, i.e., the photoreceptors consisting of rods and cones. The dysfunction and/or loss of these RPE cells play a critical role in the loss of the photoreceptors and hence blindness in AMD. Recent advances in research show promise in new therapies to treat AMD. Human embryonic stem cells, gene therapies, complement factors, and viral vectors are under development with early stage animal studies and/or clinical trials. Some of these treatments require administration of the cells into targeted areas of the eye including the sub-retinal space or the suprachoroidal space with exquisite control over position, volumetric delivery rate, and/or total volume.

Aesthetic Medicine: The goals in aesthetic medicine are generally to improve external perception of a person's skin and or external features. There are multiple therapies that require controlled injection of therapeutic agents to achieve their targeted effects.

Neurotoxins: For example, botulinum toxin may be used to temporarily deaden nerves to prevent a person from using muscle groups that create facial wrinkles. The two common areas are the frontalis muscles of the forehead and around the mouth. Botulinum toxin is a low viscosity fluid that requires controlled delivery over volume and precise control over the position so that treatment is limited to a target area to prevent unintended consequences to the patient.

These neurotoxins are low viscosity and are injected with small syringes and/or needles, and require fine motor and position control on the part of the clinician to prevent injection of too much fluid volume or injection into the wrong area, both of which may cause damage to a patient. Because the cross-sectional area of the small syringes are relatively small, high injection pressures may be generated with low plunger forces so control over the injection volume and rate is reduced.

Dermal fillers: Highly viscous fluids, such as hyaluronic acid, may be injected into a patient's skin to increase the volume of the skin, to push out wrinkles, fill voids left by acne scarring or surgical removal of tumors, give volume to lips, and/or fill the upper cheeks. These are typically injected using relatively large syringes that require high plunger forces that the surgeon must manually apply. Simultaneously, the clinician must maintain positional accuracy to hit the desired location and control the delivery rate to minimize patient discomfort.

Fat grafting: In some cases, fat is harvested from one portion of a patient's body, purified and concentrated, and then injected as a filler into an area targeted for cosmetic improvement. Grafted fat may be used as a filler material in the same manner as the other dermal fillers. In "micro" fat grafting, small amounts are used for facial improvements, while more general fat grafting may be used to increase the size of breasts or buttocks. The injection of this material has the same challenges as other dermal fillers as it requires relatively high injection pressures with good control over position and delivery rate.

Figure 2A:
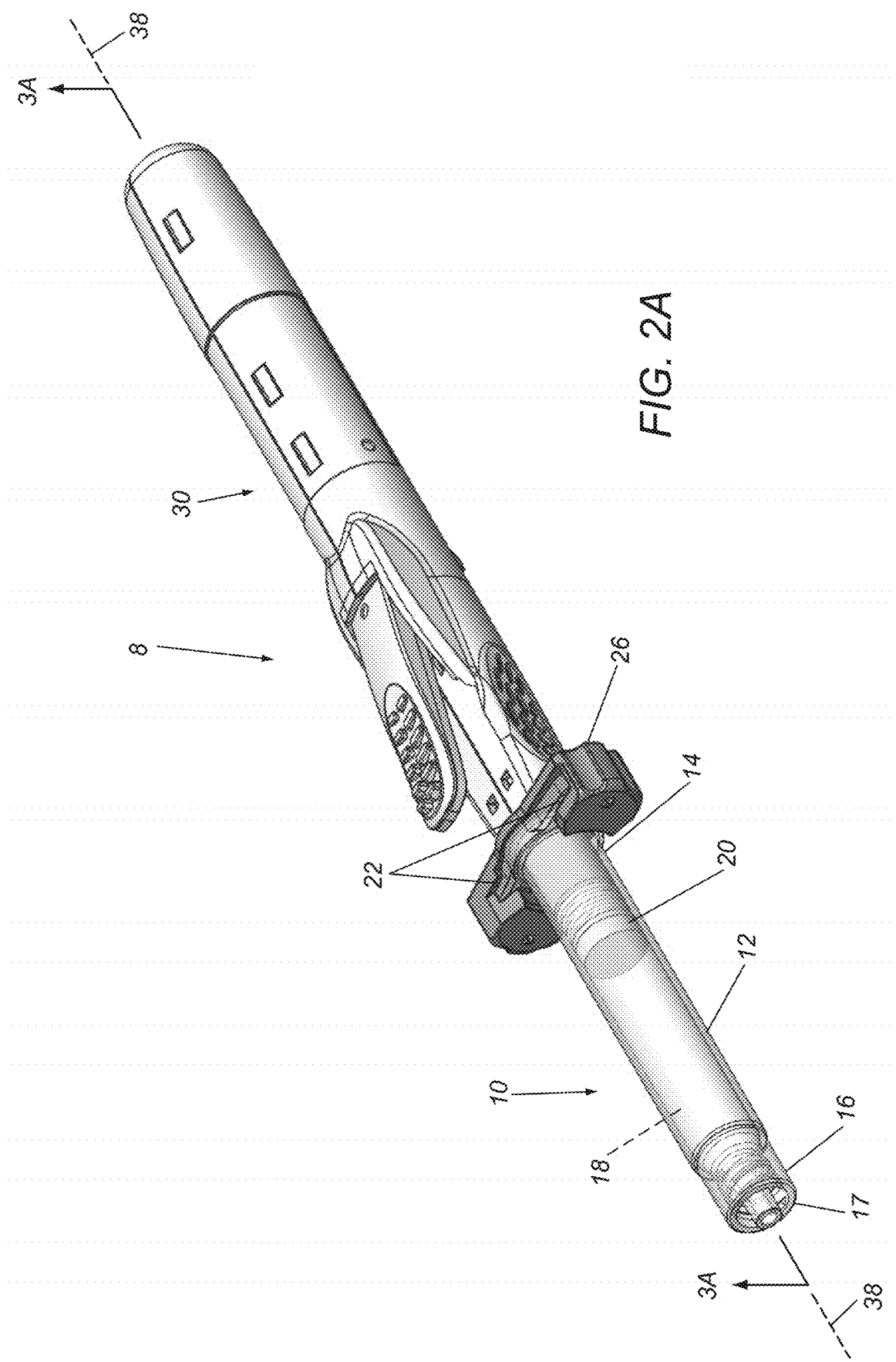

Turning to FIGS. 2A-3B, an exemplary embodiment of a syringe device 8 is shown that includes a syringe cartridge 10 and a syringe driver 30, which may include components and/or perform similar to any of the embodiments described herein. Generally, the syringe cartridge 10 includes a cartridge housing 12 including an open proximal end 14, a closed distal end 16, and defining an interior volume 18 within which a delivery piston 20 is slidably received. The proximal end 14 may include one or more connectors for engaging cooperating connectors on the syringe driver 30 to couple the cartridge 10 to the driver 30. For example, as shown in FIGS. 2A and 2B, the housing 12 may include a pair of flanges 22 on the proximal end 14 that may be coupled to a bracket, latch, or other cooperating connector(s) 26 on the driver 30.

In one embodiment, the connector 26 may receive and/or otherwise engage the flanges 22 such that the cartridge 10 is substantially permanently coupled to the driver 30. Alternatively, the connector 26 may allow the cartridge 10 to be removably coupled to the driver 30, e.g., to allow different combinations of cartridges and drivers to be assembled during manufacturing or immediately before use. In another alternative, the cartridge 10 may be integrated together with the driver 30 as a unitary assembly (not shown) and the flanges 22 and connector 26 may be omitted, if desired.

The cartridge 10 also includes a delivery port 17 on the distal end 16, e.g., for delivering a medicament from the interior 18 into a patient's body, e.g., during any of the procedures described elsewhere herein. For example, as shown, the delivery port 17 may include a Luer fitting or other connector for coupling a needle or cannula (not shown) to the delivery port 17. Alternatively, a needle may be permanently molded or otherwise integrated into the distal end 16 (not shown), if desired.

Figure 3A:
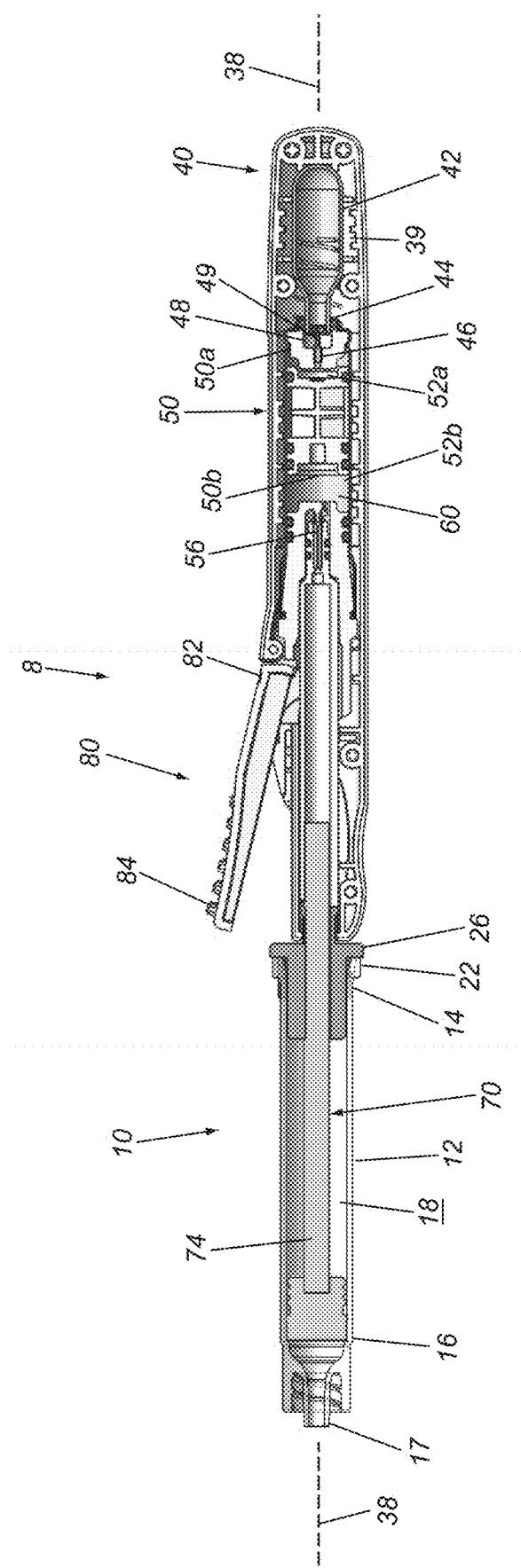
FIGS. 3A and 3B are cross-sectional views of the syringe device of FIGS. 2A and 2B, taken along planes 3A-3A and 3B-3B, respectively.
Figure 3B:
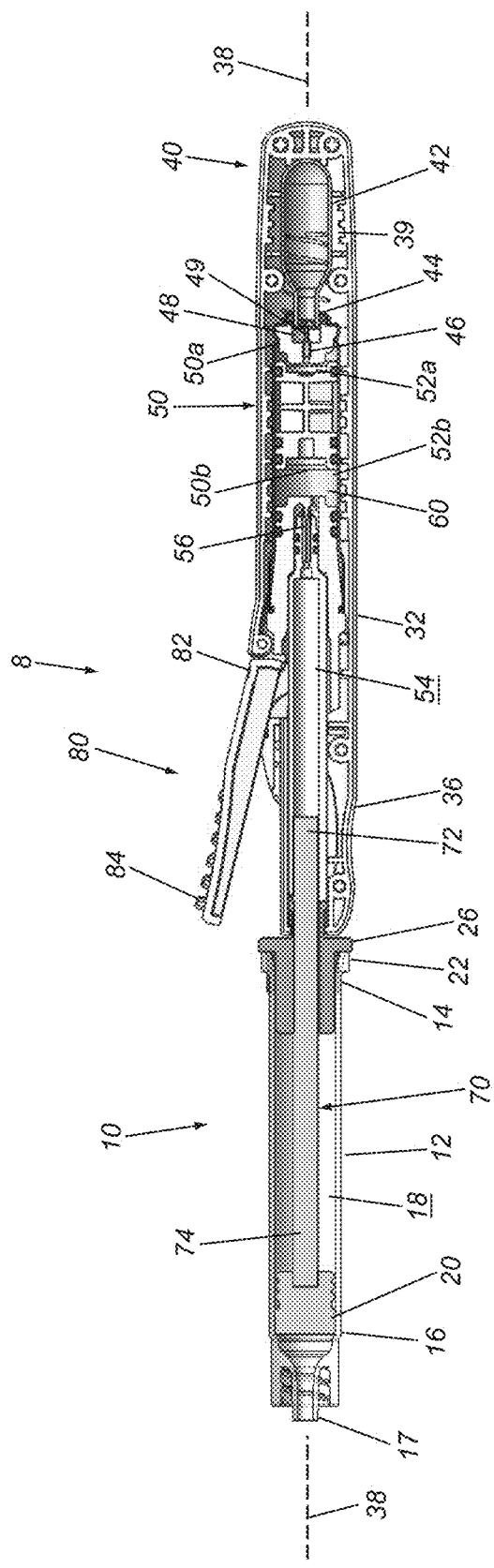

The piston 20 may be a cylindrical member including one or more seals that slidably engage the interior surface of the housing 12 to allow the piston to be directed axially within the interior 18 while providing a fluid-tight seal. For example, the piston 20 may be directed from a proximal or initial position adjacent the proximal end 14, e.g., as shown in FIGS. 2A and 3A, to a distal or advanced position adjacent the distal end 16 to deliver the fluid from the interior 18, as shown in FIGS. 2B and 3B, and described further elsewhere herein. In an exemplary embodiment, the piston 20 may include a cylindrical disc carrying one or more O-rings around an outer perimeter of the disc that engage an interior surface of the housing 12. Alternatively, the piston 20 may be formed from an elastomeric or other material as an integral body, e.g., defining one or more annular ridges that may slidingly and/or sealingly engage the interior surface of the housing 12. The materials for the piston 20 are generally compatible and/or inert with respect to the fluid contained within the interior 18.

Optionally, the piston 20 may include one or more connectors (not shown), e.g., on a proximal end or surface of the piston 20 for engaging with an actuator plunger 70 of the driver 30, as described further elsewhere herein. For example, in one embodiment, the piston 20 may simply include a recess 21 in its proximal end for receiving a distal end 74 of the actuator plunger 70, e.g., such that distal advancement of the plunger 70 causes distal advancement of the piston 20. Alternatively, the piston 20 and/or distal end 74 of the plunger 70 may include one or more detents, barbs, and/or other locking elements (not shown) that secure the distal end 74 to the piston 20 such that piston 20 follows all axial movement of the plunger 70.

With particular reference to FIGS. 3A and 3B, the syringe driver 30 generally includes an outer housing 32 including an enclosed proximal end 34 and a distal end 36 including the connector 26, defining a central longitudinal axis 38 therebetween, and including various cavities, recesses, and conduits for containing components of the driver 30, e.g., aligned along or offset from the axis 38, as desired. Generally, the housing 32 includes an energy storage device 40, an actuator or accumulator piston 50 movable within an accumulator chamber 52 of the housing 32, a substantially incompressible pressurized fluid 60, a plunger 70 hydraulically coupled to the pressurized fluid 60, and an actuator 80 for advancing the plunger 70 from the distal end 36 of the housing 32 in response to the pressurized fluid 60 to deliver fluid from the interior 18 of the syringe cartridge 10 in a desired manner, as described elsewhere herein.

In the exemplary embodiment shown, the energy storage device 40 includes a canister 42 of pressurized gas including an outlet 44 communicating with a flow path 46 and a proximal region 52a of the accumulator chamber 52 within which the accumulator piston 50 is slidably disposed. Optionally, the canister 42 may be provided within a cavity 39 of the housing 32 during manufacturing and/or assembly of the driver 30, e.g., such that the canister 42 is substantially permanently contained within the housing 32. Alternatively, the housing 32 may include a removable cap (not shown), e.g., at the proximal end 34, allowing the canister 42 to be inserted into the cavity 39 before use and/or allowing the canister 42 to be removed and replaced with a new canister, if desired, by removing the cap, inserting a canister, and reattaching the cap.

In the embodiment shown, a carriage 48 may be provided within the housing 32 adjacent the chamber 39 carrying a pin 49. When the canister 42 is loaded into the cavity 39 (e.g., during manufacturing or before use), the pin 49 may be disposed adjacent a septum (not shown) at the outlet 44 of the canister 42, as shown in FIG. 3A. Optionally, the carriage 48 may be slidably disposed within the housing 32, e.g., such that initial activation of the actuator 80, causes the carriage 48 and pin 49 to move axially, e.g., from an original or distal position shown in FIG. 3A proximally towards the canister 42 to a proximal position shown (not shown), thereby puncturing the septum with the pin 49 and allowing gas to escape from the canister 42, e.g., into flow path 46 and proximal region 52a of the accumulator chamber 52.

Optionally, a spring or other biasing mechanism (not shown) may be provided within the housing 32 for biasing the carriage 48 distally towards the distal position. Thus, when the actuator 80 is released, the carriage 48 may automatically return to the distal position and the pin 49 may be withdrawn from the septum after puncturing the septum. Alternatively, the carriage 48 may remain in the proximal position and the pin 49 and septum may be configured to allow gas to escape from the canister 42 around the pin 49 into the flow path 46. In another alternative, the carriage 48 may be stationary and the canister 42 may be movable, e.g., during initial activation of the actuator 80 and/or during loading of the canister 42, to open the septum and deliver pressurized gas into the fluid path 46 and proximal region 52a. Once the canister 42 is opened, gas may be delivered through one or more passages of the housing 32 to pressurize an incompressible fluid to advance the plunger 70, as described further elsewhere herein.

In an exemplary embodiment, the canister 42 may contain a pressurized compressible fluid, e.g., a two-phase or one-phase gas, such as carbon dioxide, argon, or nitrogen, such that compressible gas from the canister 42 applies a predetermined pressure to the flow path 46 and the accumulator piston 50. Additional information regarding canisters that may be included in the syringe drivers herein may be found in U.S. application Ser. No. 15/064,464, filed Mar. 8, 2016, the entire disclosure of which is expressly incorporated by reference herein. In alternative embodiments, instead of the canister 42, the energy storage device 40 may include a mechanical spring, e.g., configured to apply a predetermined force profile, e.g., a substantially constant or variable force, to the accumulator piston 50 upon actuation of the syringe driver 30.

With continued reference to FIGS. 3A and 3B, the accumulator piston 50 is a generally cylindrical body slidably disposed within the accumulator chamber 52, thereby dividing the accumulator chamber 52 into a proximal region 52a communicating with the flow path 46 and a distal region 52b containing the incompressible fluid 60. The accumulator piston 50 may include one or more O-rings or other seals (not shown) to provide a substantially fluid-tight seal to isolate the proximal and distal regions 52a, 52b and the respective fluids therein, while allowing the accumulator piston 50 to move axially within the chamber 52.

The distal region 52b communicates via a valve 56 with a plunger chamber 54 (best seen in FIG. 3B) within which the proximal end 72 of the actuator plunger 70 is disposed. The actuator 80 is coupled to the valve 56 for selectively opening the valve 56, to provide a flow controller that allows incompressible fluid 60 within the distal region 52b to pass through the valve 56 into the plunger chamber 54, thereby advancing the plunger 70 distally in a desired manner. In exemplary embodiments, the fluid 60 may be an incompressible liquid, such as silicone oil, propylene glycol, glycerin, saline, water, or other substantially incompressible fluids.

The actuator 80 may include any type of actuator configured to provide controllable actuation of the output of mechanical energy from the energy storage device 40. For example, in some embodiments, the actuator 80 may include a mechanical or electronic button or lever that allows a user to control output of mechanical energy from the energy storage device 40. For example, as shown, the actuator 80 may be a lever including a first end 82 pivotally coupled to the housing 32 and a second free end 84 that may be manipulated by the user to open the valve 56. In the exemplary embodiments described further below, the actuator 80 and/or valve 56 may include one or more additional components for applying a predetermined force profile to the actuator plunger 70, e.g., for opening the valve 56 in a desired manner, e.g., similar to any of the embodiments described elsewhere herein.

The accumulator piston 50 is configured to move slidably along the longitudinal axis 38 of the device 8 within the accumulator chamber 52. As such, the accumulator piston 50 includes a first or proximal surface 50a exposed to pressure from the compressed gas delivered from the canister 42 into the fluid path 46 and proximal region 52a, and a second or distal surface 50b exposed to the incompressible fluid 60 within the distal region 52b. In this manner, the actuator piston 50 and chamber 52 may provide an accumulator that may apply a predetermined pressure and/or force to the incompressible fluid 60 to cause the incompressible fluid 60 to pass through the valve 56 into the plunger chamber 54 to advance the plunger 70 in a desired manner, e.g., according to a force, pressure, and/or other profile, e.g., as described with respect to the exemplary embodiments described further herein.

In addition, the syringe driver 30 include one or more brackets, latches, and/or other connectors 26 on the distal end 36 of the driver housing 32, e.g., for permanently and/or removably coupling the driver 30 to a syringe cartridge 10, as described elsewhere herein.

During use, if the cartridge 10 and driver 30 portions are not already preassembled, a user may select an appropriate cartridge 10 and driver 30 for a given application, e.g., a cartridge 10 providing a desired therapeutic and/or diagnostic fluid and/or volume, and a driver 30 providing a desired force, pressure, and/or other performance profile for delivering the fluid from the selected cartridge 10. The flanges 22 and/or other connectors on the cartridge 10 may be engaged with the bracket 26 and/or other connectors on the distal end 36 of the driver 30, e.g., to thereby engage the distal end 74 of the actuator plunger 70 with the piston 20 within the cartridge 10. During this assembly, the distal end 74 of the actuator plunger 70 may be received within the recess 21 in the actuator piston 20 and/or may engage cooperating connectors (not shown), if desired. A needle, cannula, or other delivery device (not shown) may be coupled to the connector 17 on the cartridge 10, e.g., after assembly. The assembled device 8 may then be ready to deliver one or more agents within the interior 18 of the cartridge 10 into a patient's body, e.g., any of the agents and/or procedures described elsewhere herein.

In an exemplary procedure, when the actuator 80 is initially activated, the pin 49 may open the septum at the outlet 44 of the canister 42, and gas from the canister 42 may be released and/or expand into the fluid path 46 and proximal region 52a, thereby pressurizing the actuator piston 50 and/or incompressible fluid 60 in the distal region 52b. Further actuation of the actuator 80 causes the pressurized fluid 60 to flow through the valve 56 into the piston chamber 54, thereby advancing the actuator plunger 70, and consequently the delivery piston 20, distally to deliver fluid within the interior 18 through the delivery port 17 of the cartridge 10. In exemplary embodiments, such as those described below, the valve 56 may be a needle valve or a pressure-compensated flow control valve, and/or may include a pressure regulator and/or other suitable element for limiting and/or controlling flow of the incompressible fluid 60. In addition or alternatively, flow of the incompressible fluid 60 may be controlled by modulating pressure of the pressurized gas applied to the fluid, e.g., by including one or more flow control elements (not shown) in the fluid path 46 and/or by modifying the resistance of the accumulator piston 50 to axial movement at different locations within the accumulator chamber 52. As a result, in exemplary embodiments, the output flow of the incompressible fluid 60 when the actuator 80 and valve 56 are activated may be linear, exponential, polynomial, or other desired profile.

Figure 4:
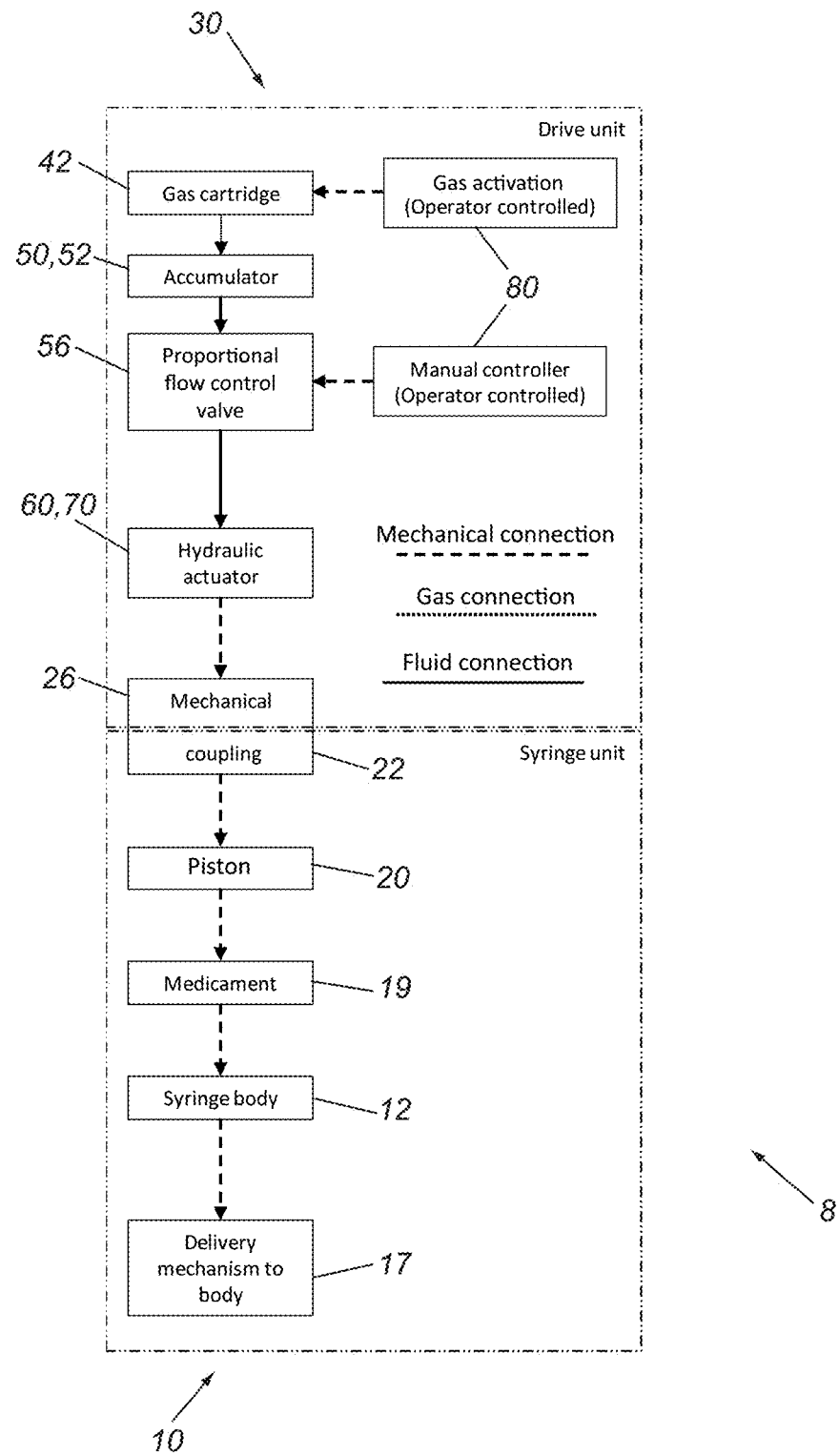
FIG. 4 is a schematic of an exemplary embodiment of a syringe device including a self-powered syringe driver that provides a simple proportional drive.

Turning to FIG. 4, a schematic of an exemplary embodiment of a syringe device 8 is shown, generally similar to that shown in FIGS. 2A-3B, e.g., including a syringe cartridge 10 and syringe driver 30. As shown, the cartridge 10 may include a housing 12 including a delivery piston 20 for delivering a medicament 19 (e.g., within an interior 18 of the housing 12, as described with reference to FIGS. 2A-3B) via a delivery mechanism, e.g., delivery port 17, similar to the device 8 shown in FIGS. 2A-3B.

As described elsewhere herein, the cartridge 10 and driver 30 may include one or more cooperating connectors 22, 26 that provide a mechanical coupling for permanently and/or removably coupling a desired cartridge 10 to a desired driver 30. For example, a user may select a desired driver 30 that provides a desired delivery profile, e.g., proportional delivery (or any of the other profiles described elsewhere herein), and/or a desired cartridge 10, e.g., including a desired medicament 19, volume, and the like, and couple them together before delivery of the medicament 19. The resulting device 8 may be a single-use device, i.e., where, upon delivery of the medicament 19, the entire device 8 is disposed. Alternatively, after delivery, the cartridge 10 may be removed and disposed, and the driver 30 may be sterilized and/or otherwise processed for use in a future procedure with a new cartridge.

During use, the syringe driver 30 may provide proportional control of fluid flow from the cartridge 10, e.g., such that the user may apply an actuation force to the actuator (manual controller) 80 that opens the valve 56, e.g., a needle valve, to generate correspondingly proportional speed control to the plunger 70 and, thus, flow control of the medicament 19 from the interior 18 of the cartridge 10. In this manner, the user may intuitively deliver a desired volume and/or flow rate of the medicament 19 from the cartridge 10 into a patient's body with the force applied to the actuator 80 being much less than and/or independent of the resulting force applied to the plunger 70 and piston 20, which may facilitate precise delivery of the medicament 19.

The accumulator, e.g., actuator piston 50 and chamber 52, may convert gas pressure from the canister 42, which may be substantially continuous and/or constant, to hydraulic pressure that is applied to the plunger 70. Thus, the incompressible fluid 60 may transmit a force to the plunger 70, e.g., to eliminate hysteresis and/or allow the user to increase and/or decrease the flow rate and, thus, the speed available from the driver 30 in a desired manner.

Figure 5:
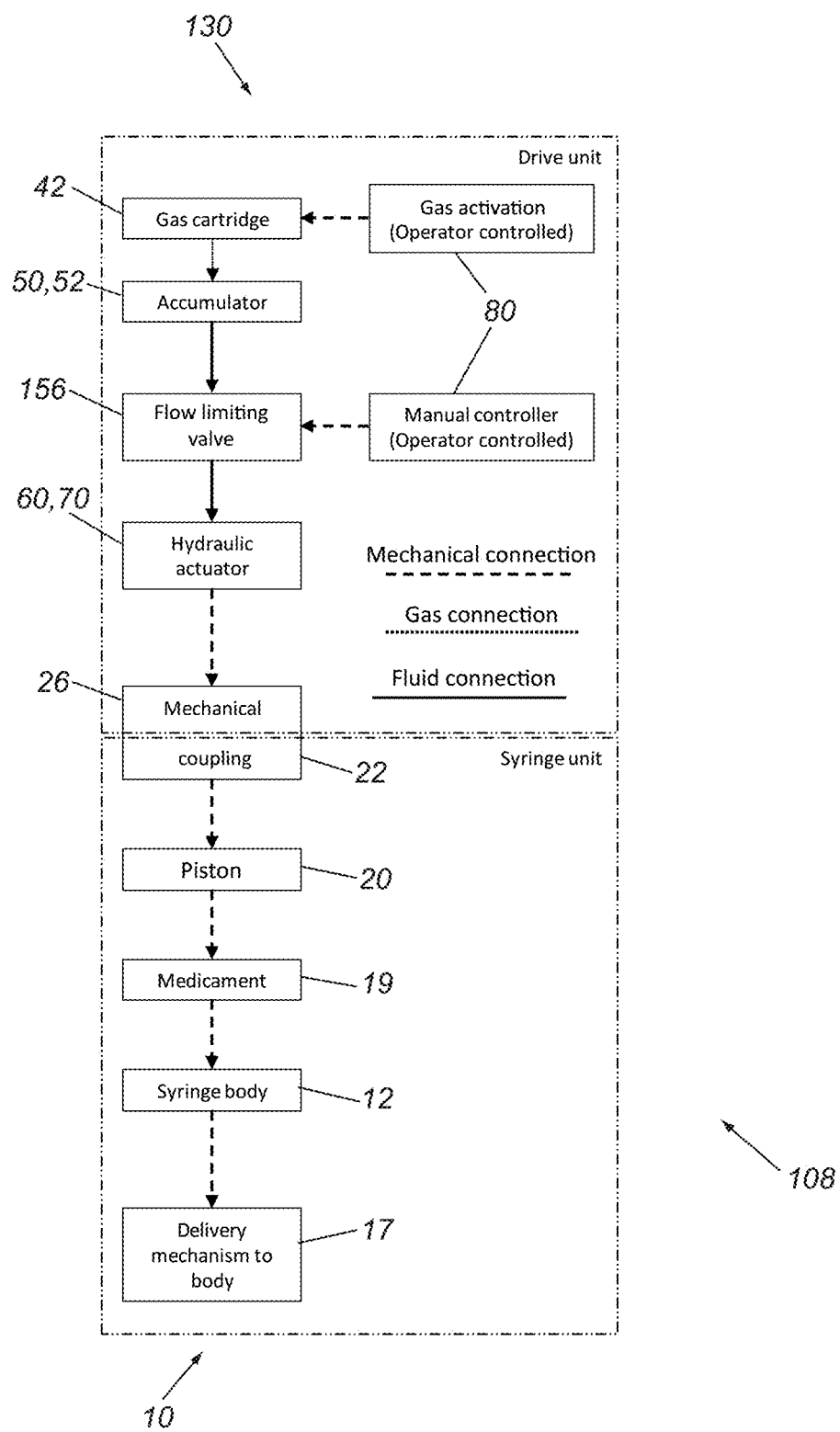
FIG. 5 is a schematic of another exemplary embodiment of a syringe device including a self-powered syringe driver that provides a simple flow limiting drive.

Turning to FIG. 5, a schematic of another exemplary embodiment of a syringe device 108 is shown that includes a syringe cartridge 10 (e.g., similar to any of the previous embodiments) and syringe driver 130 that provides a flow limiting drive. For example, as shown, the cartridge 10 may include a housing 12 including a delivery piston 20, medicament 19 contained within an interior of the housing 12, and an outlet port or other delivery mechanism 17, similar to other embodiments.

The driver 130 may include similar components to the previous components, e.g., a canister 42 containing compressible gas communicating with an accumulator, e.g., actuator piston 50, and an actuator 80, although in this embodiment, the valve 156 is a flow limiting valve. The actuator 80 causes the flow limiting valve 156 to open to deliver incompressible fluid 60 to the actuator plunger 70, with the flow limiting valve 156 limiting the speed of the actuator 80 and, thereby, limiting flow of the medicament 19 from the cartridge 10 into a patient's body to a predetermined maximum flow rate. Thus, this driver 130 may enable volumetric flow limiting below a desired maximum flow rate, which may useful for micro-fluidic delivery, e.g., during sub-retinal injection of gene and stem cell therapies. Such limitations on flow of the medicament may also reduce patient pain, e.g., associated with rapid volumetric expansion that may occur with relative high rate fluid delivery.

Figure 6:
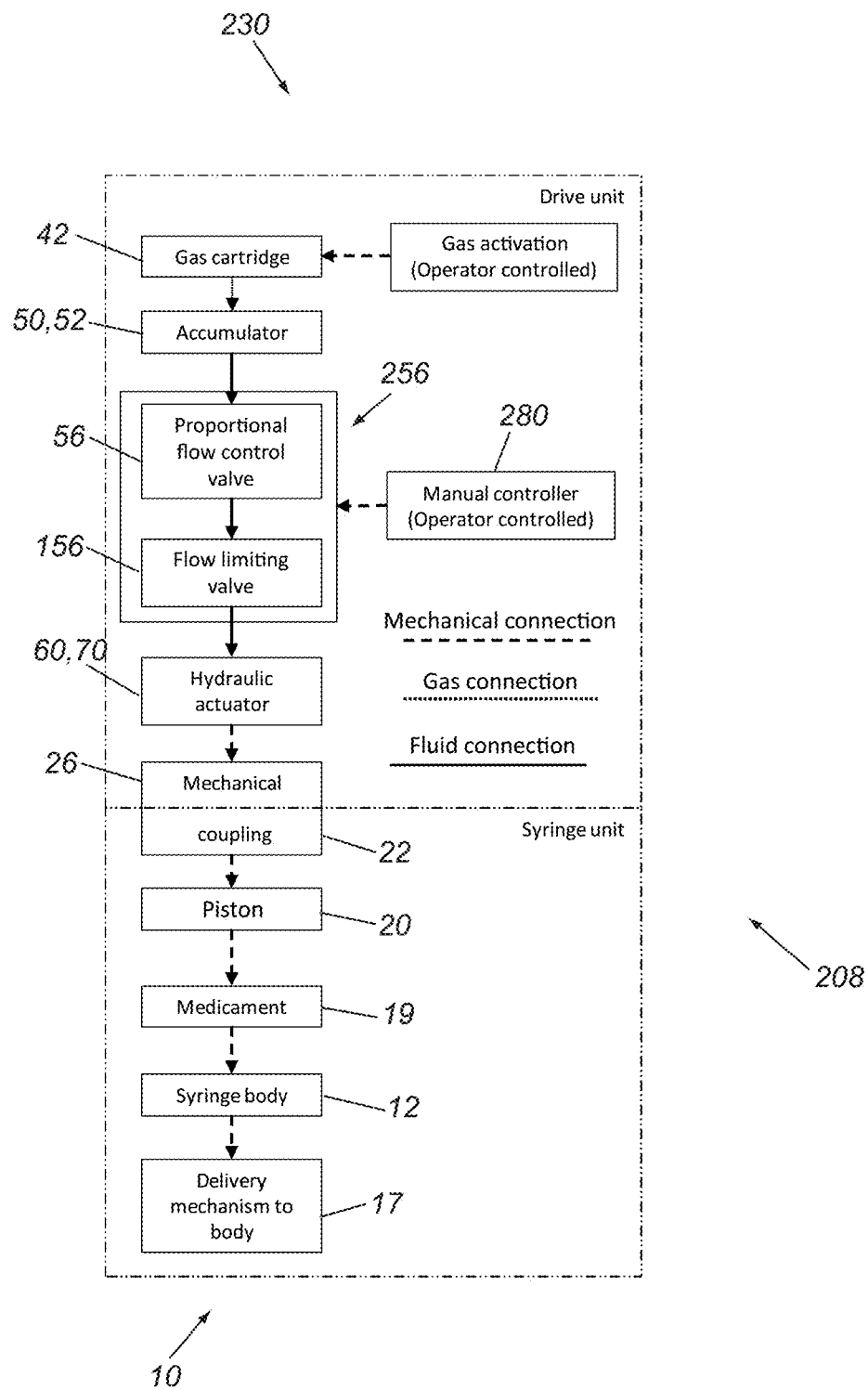
FIG. 6 is a schematic of yet another exemplary embodiment of a syringe device including a self-powered syringe driver that provides a proportional/flow limiting drive.

Turning to FIG. 6, a schematic of yet another exemplary embodiment of a syringe device 208 is shown that includes a syringe cartridge 10 (e.g., similar to any of the previous embodiments) and syringe driver 230 that provides both a proportional and flow limiting drive. The device 208 may operate similar to a combination of the devices 8, 108, e.g., having a valve 256 that includes both a proportional flow control valve 56, i.e., that provides a flow rate proportional to the amount of activation of the actuator 280, and a flow limiting valve 156, i.e., that limits flow from the cartridge 10 to a predetermined maximum flow rate even of the actuator 280 is activated beyond a maximum position. For example, the proportional flow control valve 56 may enable proportional control during an initial stage of actuation, while the flow limiting valve 156 may limit flow of the medicament 19 to no more than a desired maximum flow rate during a final stage of actuation.

Figure 6A:
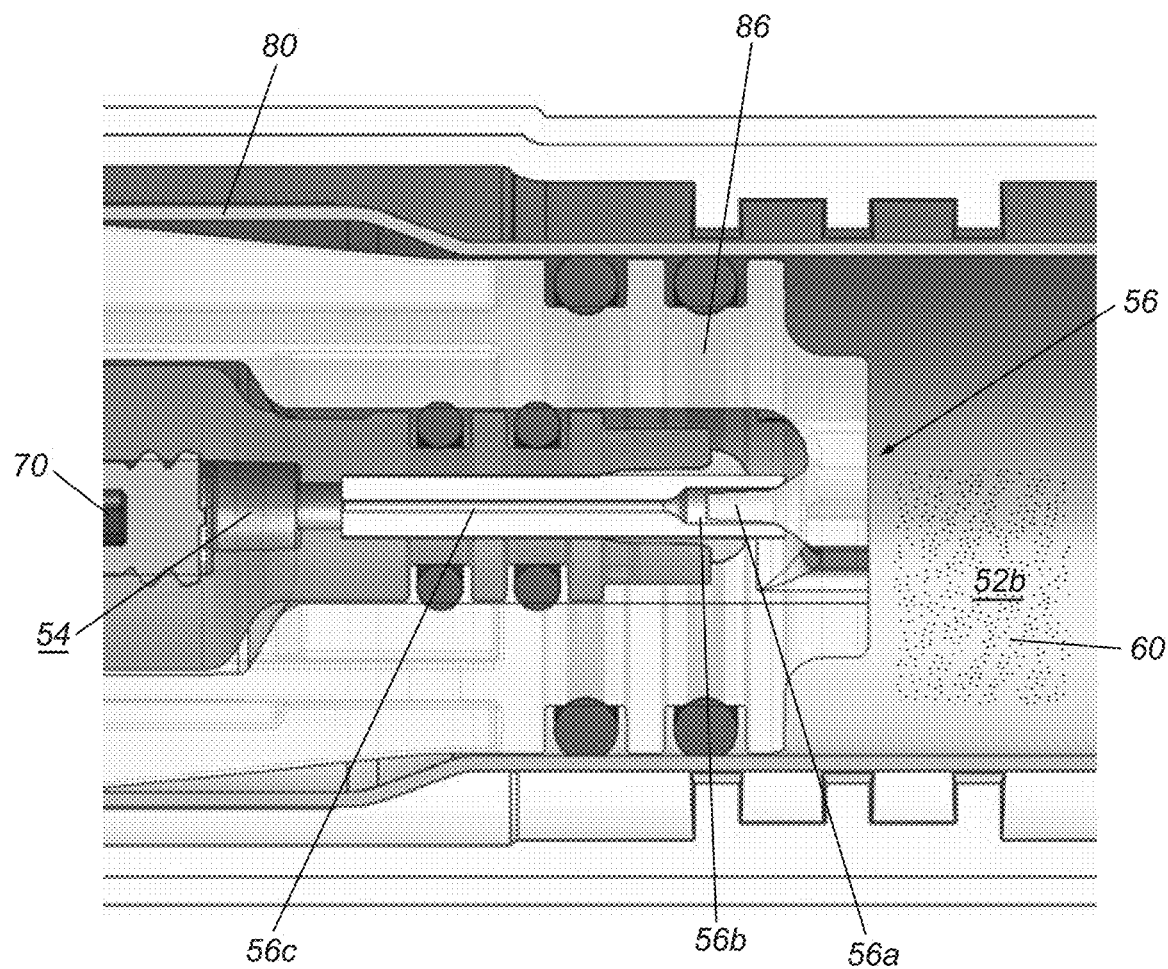
FIG. 6A is a cross-sectional detail of an example of a valve that may be included in the syringe driver of FIG. 6.

Turning to FIG. 6A, an exemplary embodiment of a flow control valve 56 that includes initial proportional control and limited flow during a final stage of actuation. As shown, the valve 56 is a needle valve including a needle or pin 56a mounted on a carriage 86 that is coupled to the actuator 80, e.g., such that activation of the actuator 80 causes the carriage 86 and, consequently, the pin 56a to move proximally. The pin 56a is received in a recess 56b that communicates with a relatively small cross-section passage 56c that communicates with the plunger chamber 54, within which the proximal end 72 of the actuator plunger 70 is received, as described elsewhere herein. In an initial or proximal position, before the actuator 80 is activated, the pin 56a engages the wall of the recess 56b, thereby preventing the fluid 60 from entering the passage 56c. As the actuator 80 is activated, the carriage 56 directs the pin 56a proximally out of the recess 56b, thereby creating an annular space around the pin 56a through which the fluid 60 may pass and enter the passage 56c and plunger chamber 54.

In the embodiment shown in FIG. 6A, the pin 56a has a tapered shape, tapering from its base distally to its tip. This configuration may provide proportional control, i.e., such that fluid 60 flows at a flow rate to cause the plunger 70 to advance at a corresponding speed to deliver the medicament 19. However, the pin 56a and recess 56b are sized such that, during the final stage of actuation, the pin 56a exits the recess 56b entirely. Fluid 60 may continue to flow into the recess 56b; however, the flow rate into the passage 56c is limited given the relatively large size of the recess 56b compared to the passage 56c, thereby limiting the flow of the fluid 60 to a predetermined maximum flow rate.

Figure 7:
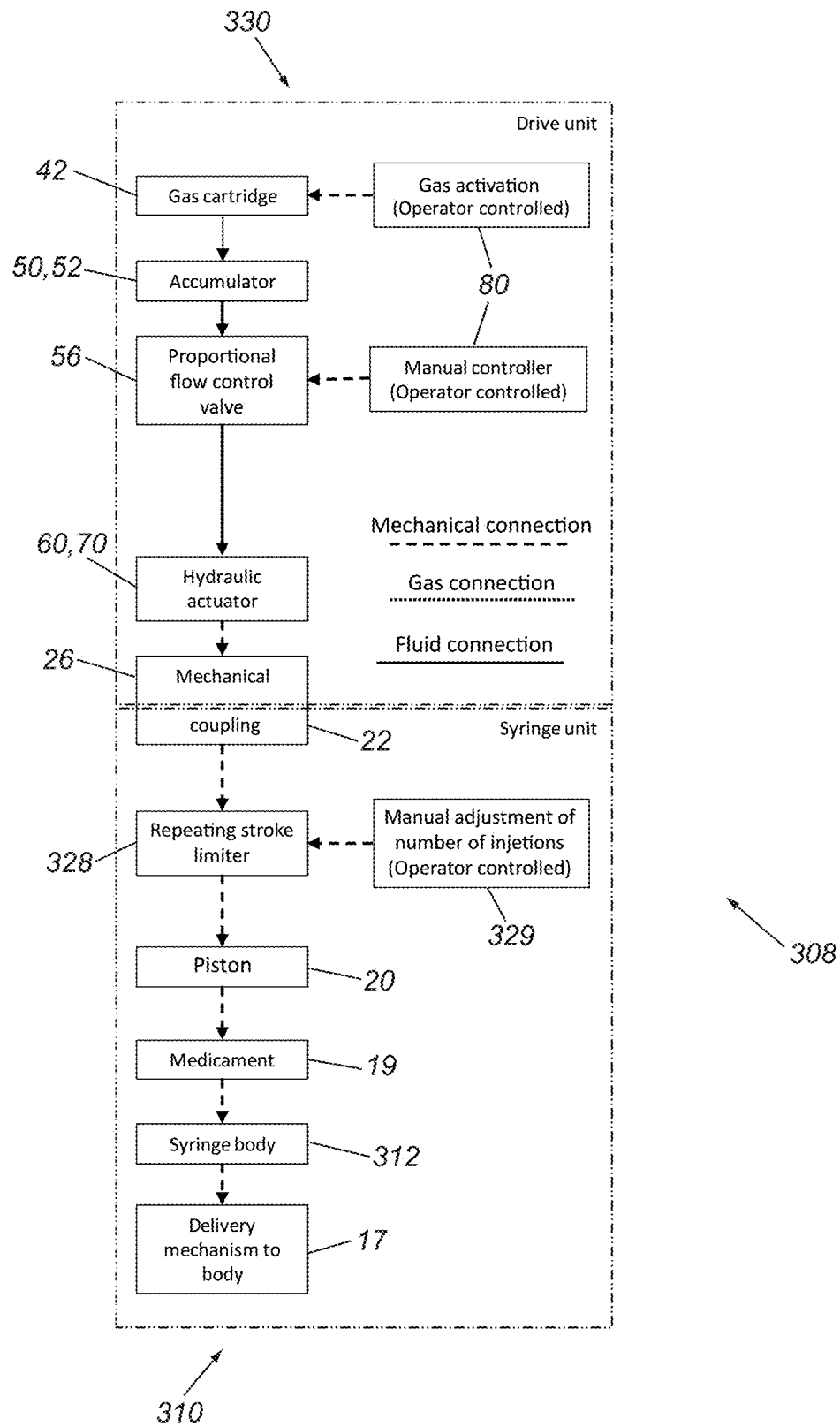
FIG. 7 is a schematic of still another exemplary embodiment of a syringe device including a self-powered syringe driver that provides an injection quantity limiting drive.

Turning to FIG. 7, a schematic of another exemplary embodiment of a syringe device 308 is shown that includes a syringe cartridge 310 and syringe driver 330. As shown, the cartridge 310 may include a housing 312 including a delivery piston 20, medicament 19 contained within an interior of the housing 312, and an outlet port or other delivery mechanism 17, similar to other embodiments. The driver 330 may include similar components to the previous components, e.g., a canister 42 containing compressible gas communicating with an accumulator, e.g., actuator piston 50, and an actuator 80 including a valve 56, which may be any of the embodiments herein. The cartridge 310 and driver 330 may include cooperating connectors 22, 26 for removably and/or permanently coupling the components together, as described elsewhere herein. Also similar to previous embodiments, the actuator 80 releases the compressible gas from the gas canister 42 to apply pressure to the accumulator piston 50, and then causes the valve 56 to open to deliver incompressible fluid 60 to the actuator plunger 70, in a desired manner.

Unlike previous embodiments, the cartridge 310 (or driver 330) may include a repeating stroke limiter 328, i.e., that limits movement of the piston 20 when the driver 330 is actuated. For example, the limiter 328 may be a mechanical device coupled to or incorporated into the cartridge 310 that allows the delivery piston 20 to be advanced a preset number of times, e.g., with each advancement delivering a desired volume of the medicament 19 from the housing 12. For example, the actuator 80 may be activated to deliver a first injection, which may deliver a desired volume, e.g., set based on how long the actuator 80 is activated. Once the actuator 80 is released, the limiter 328 may reset and allow another dose to be delivered in a second activation (and, optionally, additional subsequent activations). Optionally, the limiter 328 may include an adjustment mechanism 329 that allows the user to set the maximum number activations and corresponding injections that may delivered by the device 308.

Figure 8:
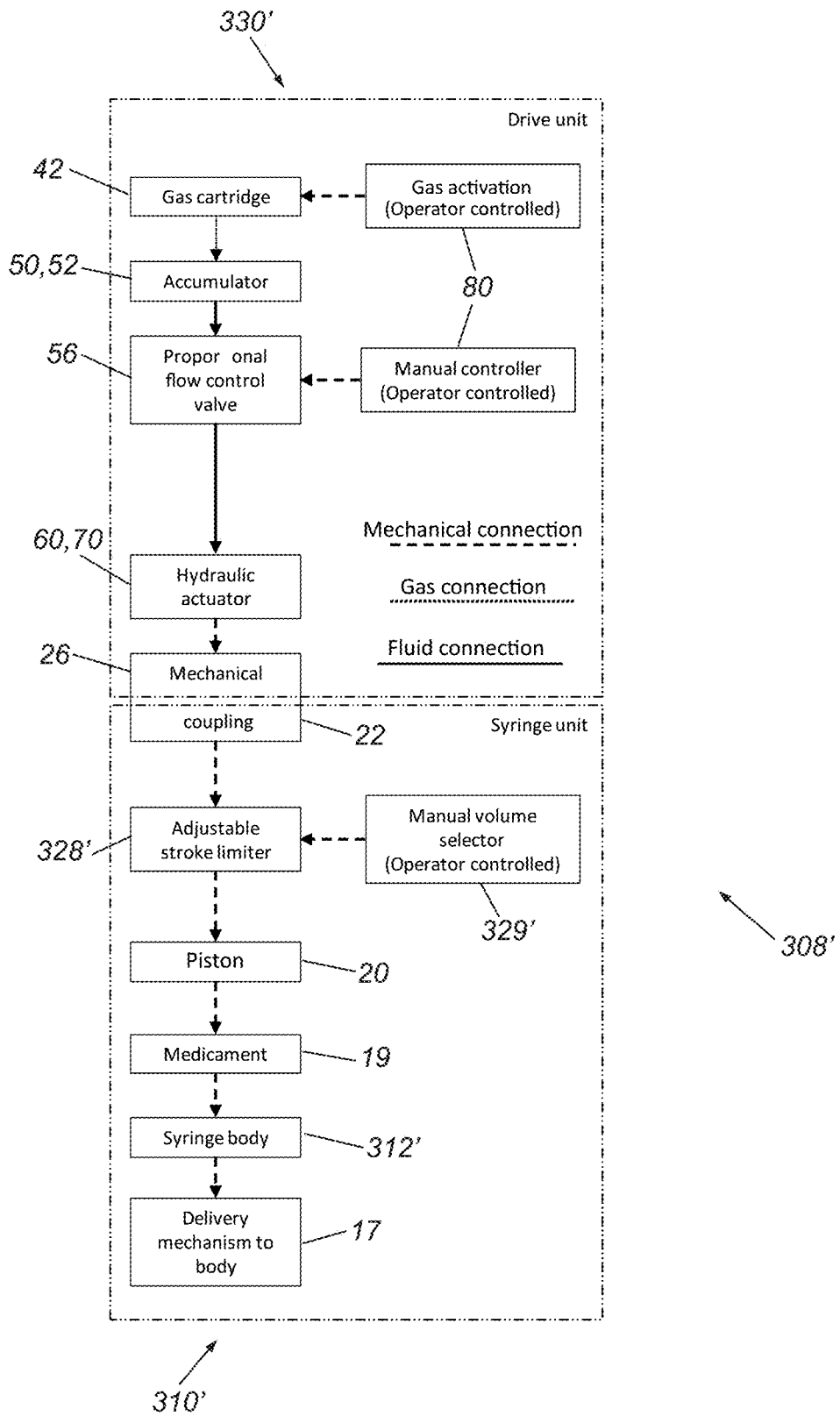
FIG. 8 is a schematic of another exemplary embodiment of a syringe device including a self-powered syringe driver that provides a volumetric flow limiting drive.

Alternatively, as shown in FIG. 8, a syringe device 308' is shown that includes a stroke limiter 328' that includes an adjustment mechanism 329' that allows a user to adjust the piston distance and volume delivered to be adjusted by the user. For example, before each activation, the user may use the adjustment mechanism 329' to set the volume for the corresponding injection. Alternatively, the adjustment mechanism 329' may only be adjusted once, e.g., such that each activation delivers the same volume of medicament 19. In a further alternative shown in FIG. 9, a syringe device 308" may be provided with a cartridge 310" (and/or driver 330") that includes both a repeating stroke limiter 328a" and an adjustable stroke limiter 328b," which may include corresponding adjustment mechanism 329a," 329b." Thus, in this embodiment, the device 308" may enable the user to deliver repetitive volumetric doses, with the number of injections and/or volume of individual injections to be set by the user at the time of use. Otherwise, devices 308,' 308" may be similar to device 308 and/or any of the other embodiments herein.

Figure 9:
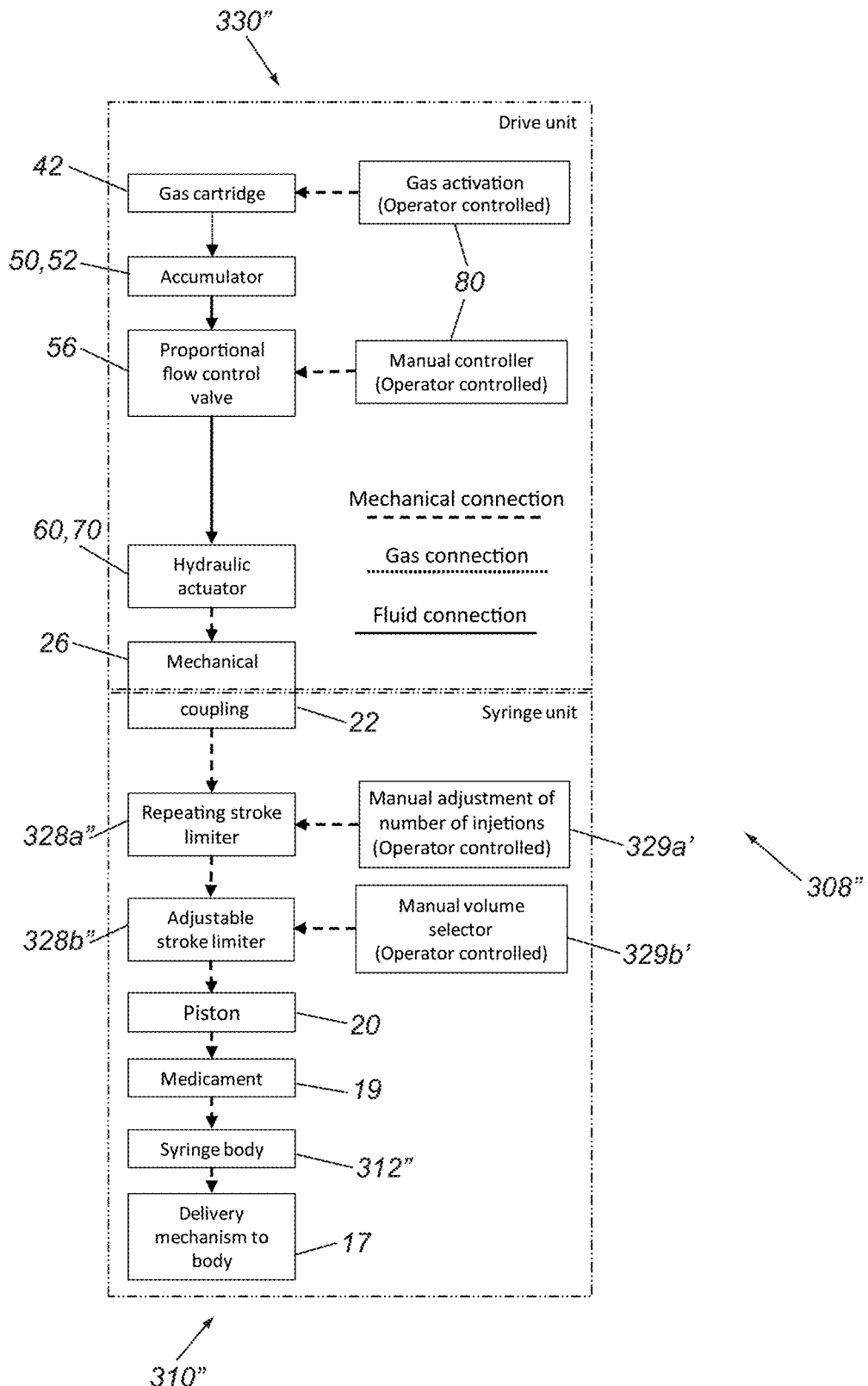
FIG. 9 is a schematic of yet another exemplary embodiment of a syringe device including a self-powered syringe driver that provides an injection quantity/dose limiting drive.

It will be appreciated that a proportional flow control valve 56 is shown in the devices 308, 308,' 308" of FIGS. 7-9, i.e., such that activation of the actuator 80 causes the incompressible fluid 60 to flow in a manner to cause proportional movement of the delivery plunger 70 and piston 20. Alternatively, the valve 56 may be replaced with any of the other embodiments herein.

Figure 10:
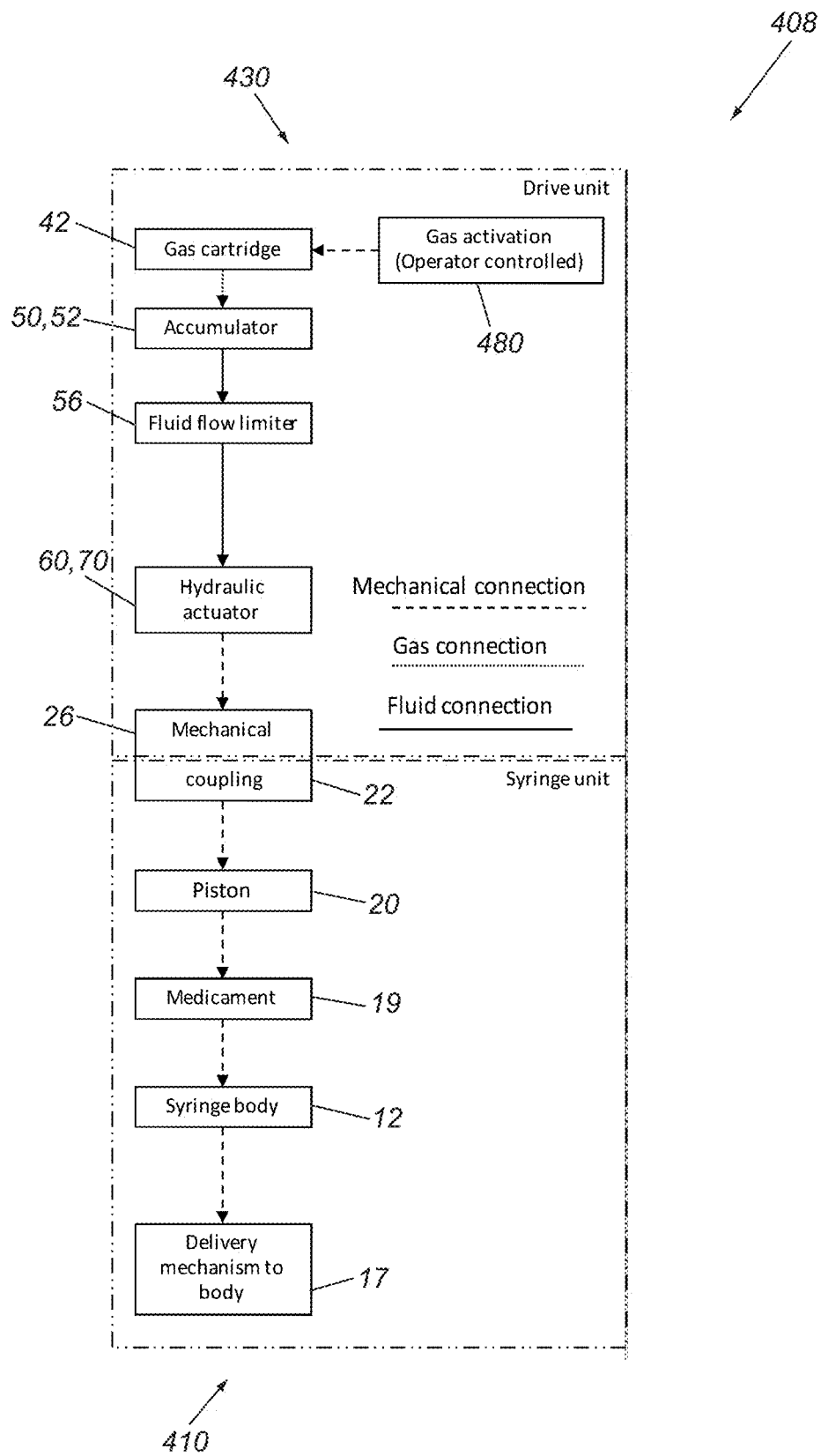
FIG. 10 is a schematic of still another exemplary embodiment of a syringe device including a self-powered syringe driver that provides a time released delivery drive.

Turning to FIG. 10, still another exemplary embodiment of a syringe device 408 is shown that includes a syringe cartridge 410 and syringe driver 430. As shown, the cartridge 410 may include a housing 12 including a delivery piston 20, medicament 19 contained within an interior of the housing 312, and an outlet port or other delivery mechanism 17, similar to other embodiments. The driver 430 may include similar components to the previous components, e.g., a canister 42 containing compressible gas communicating with an accumulator, e.g., actuator piston 50, and an actuator 480.

Unlike the previous embodiments, the actuator 480 is not coupled to a valve. Instead, the driver 430 includes a flow limiter 456 that controls flow of the incompressible fluid 60 to advance the actuator plunger 70 in a desired manner once the actuator 480 is activated. For example, when the actuator 480 is activated, compressible gas is released from the gas canister 42 to apply pressure to the accumulator piston 50, which forces the incompressible fluid 60 to flow through the flow limiter 456 to advance the plunger 70 without further action from the user. Thus, the accumulator piston 50 converts gas pressure from the canister 42 to fluid/hydraulic pressure, and the flow limiter 456 transmits forces to the plunger 70, thereby automatically advancing the delivery piston 20 and delivering medicament 19 from the housing 12 through the delivery mechanism 17 when the actuator 480 is initially activated.

The flow limiter 456, e.g., a venturi, orifice, or other element, may be fixed such that the speed of the plunger 70 and the resulting flow rate of the medicament 19 may be fixed when the actuator 480 is activated. For a plunger 70 having a preset stroke distance, a fixed flow limiter 456 may fix the time of delivery of the medicament 19 into the patient's body. Alternatively, the flow limiter 456 may be adjustable such that the user may set the flow limiter 456, e.g., between minimum and maximum speeds and/or between fixed intervals, to provide a desired flow rate and corresponding time of delivery of the medicament 19. In a further alternative, the flow rate of the incompressible fluid 60 may be adjusted by changing the viscosity of the fluid 60.

Similar to the previous embodiments, the cartridge 410 and driver 430 may be removably and/or permanently coupled together, using cooperating connectors 22, 26. For example, the syringe cartridge 410 may be preloaded separate from the driver 430, e.g., using conventional methods, and then coupled to the driver 430 immediately before use. Alternatively, the cartridge 410 may be loaded while coupled to the driver 430.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A device for delivering a medicament into a patient's body, comprising:
   a syringe cartridge comprising a housing including a proximal end, a distal end, and defining an interior, the cartridge further comprising a piston slidably disposed within the interior for delivering a medicament within the interior through a port in the distal end; and
   a syringe driver comprising a plunger for advancing the piston within the interior of the housing, a source of pressurized fluid, a valve, and an actuator member coupled to the valve for selectively opening a flow path from the source to the plunger to control flow of the pressurized fluid to advance the plunger to deliver medicament from the interior of the housing at a desired rate,
   wherein the source of pressurized fluid comprises a canister of compressible gas, and
   wherein the valve comprises a pin received within a recess communicating with the flow path, the pin and recess configured to provide proportional control during initial activation of the actuator and to limit flow of the fluid along the flow path during a final stage of activation to limit advancement of the plunger while the actuator remains activated, thereby limiting flow of the medicament to a maximum flow rate during the final stage.

2. The device of claim 1, wherein the source of pressurized fluid further comprises a chamber containing incompressible fluid and a piston disposed between the chamber and the canister of pressurized gas to apply a predetermined pressure to the incompressible fluid within chamber when the pressurized gas is released from the canister.

3. The device of claim 2, wherein the incompressible fluid is a viscous fluid.

4. The device of claim 1, further comprising one or more connectors for coupling the syringe driver to the proximal end of the syringe cartridge.

5. The device of claim 4, wherein the one or more connectors comprise one or more flanges on the proximal end of the housing and a latch or bracket on the syringe driver for receiving the one or more flanges.

6. The device of claim 4, wherein the one or more connectors comprise a receiver on the syringe driver for receiving the proximal end of the syringe cartridge.

7. The device of claim 4, wherein the one or more connectors removably couple the syringe driver to the syringe cartridge.

8. The device of claim 4, wherein the one or more connectors permanently couple the syringe driver to the syringe cartridge.

9. The device of claim 1, further comprising a repeating stroke limiter that limits a number of doses of the medicament that may be delivered from the syringe cartridge.

10. The device of claim 9, wherein the repeating stroke limiter comprises an adjustment mechanism that is adjustable by a user to set the number of doses.

11. The device of claim 1, further comprising a volumetric stroke limiter that limits a distance the delivery piston can travel when the actuator is activated to limit a volume of the medicament that may be delivered from the syringe cartridge.

12. The device of claim 11, wherein the volumetric stroke limiter comprises an adjustment mechanism that is adjustable by a user to set the volume of the medicament delivered when the actuator is activated.

13. The device of claim 1, wherein the source of pressurized fluid further comprises a substantially incompressible liquid.

14. The device of claim 13, wherein the liquid comprises silicone, glycerin, saline, or water.

15. The device claim 1, wherein the valve is configured to control flow along the flow path to provide proportional control of a speed at which the plunger advances and the corresponding flow rate of the medicament.

16. The device of claim 1, wherein the actuator and valve provide a flow controller that provides an output flow of the fluid to the plunger that is one of linear, exponential, and polynomial relative to the pressure applied by the pressurized gas.

17. The device of claim 1, wherein the medicament comprises a viscous fluid.

18. A device for delivering a medicament into a patient's body, comprising:
   a syringe cartridge comprising a housing including a proximal end, a distal end, and defining an interior containing a viscous medicament, the cartridge further comprising a piston slidably disposed within the interior for delivering the medicament within the interior through a port in the distal end; and
   a syringe driver comprising a plunger for advancing the piston within the interior of the housing, a source of pressurized fluid, a valve, and an actuator member coupled to the valve for selectively opening a flow path from the source to the plunger to control flow of the pressurized fluid to advance the plunger to deliver medicament from the interior of the housing at a desired rate, wherein the valve comprises a pin received within a recess communicating with the flow path, the pin and recess configured to provide proportional control during initial activation of the actuator and to limit flow of the fluid along the flow path during a final stage of activation to limit advancement of the plunger while the actuator remains activated, thereby limiting flow of the medicament to a maximum flow rate during the final stage.

19. The device of claim 1, wherein the pin is mounted on a carriage coupled to the actuator such that activation of the actuator causes the carriage and the pin to move proximally, and wherein the pin has a tapered shape, tapering from its base distally to its tip to provide proportional control.

20. The device of claim 19, wherein the pin is received in a recess that communicates with a relatively small cross-section passage that communicates with a plunger chamber within which a proximal end of the plunger is received, and wherein the pin and recess are sized such that, during the final stage of actuation, the pin exits the recess entirely, and the flow rate into the passage is limited given the relatively large size of the recess compared to the passage, thereby limiting the flow of the fluid into the plunger chamber to a predetermined maximum flow rate.

21. The device of claim 1, wherein the source of pressurized fluid further comprises a carriage slidably disposed within a driver housing of the syringe driver such that initial activation of the actuator causes the carriage and a pin carried on the carriage to move axially from an original or distal position towards the canister to a proximal position, thereby puncturing a septum of the canister with the pin and allowing gas to escape from the canister into a proximal region of the chamber.

22. The device of claim 21, further comprising a spring or other biasing mechanism within the driver housing of the syringe driver for biasing the carriage distally towards the distal position such that, when the actuator is released, the carriage automatically returns to the distal position and the pin is withdrawn from the septum after puncturing the septum.

* * * * *